US00PP12944P2

(12) United States Plant Patent
Hanes

(10) Patent No.: US PP12,944 P2
(45) Date of Patent: Sep. 10, 2002

(54) GERANIUM PLANT NAMED 'AMRI LIGHT PINK SPLA II'

(75) Inventor: Mitchell Eugene Hanes, Morgan Hill, CA (US)

(73) Assignee: Goldsmith Plants Inc., Gilroy, CA (US)

( * ) Notice: Subject to any disclaimer, the term of this patent is extended or adjusted under 35 U.S.C. 154(b) by 39 days.

(21) Appl. No.: 09/802,869

(22) Filed: Mar. 12, 2001

(51) Int. Cl.[7] ..... A01H 5/00
(52) U.S. Cl. ..... Plt./328
(58) Field of Search ..... Plt./324, 328, 325

*Primary Examiner*—Bruce R. Campell
*Assistant Examiner*—June Hwu
(74) *Attorney, Agent, or Firm*—Rothwell, Figg, Ernst & Manbeck

(57) ABSTRACT

A geranium cultivar particularly distinguished by dark green foliage, light pink flower color, and semi-double flowers on large umbels, fast rooting and exhibits vigorous growth.

1 Drawing Sheet

GENUS AND SPECIES

*Pelargonium hortorum.*

VARIETY DENOMINATION

Figure 1:
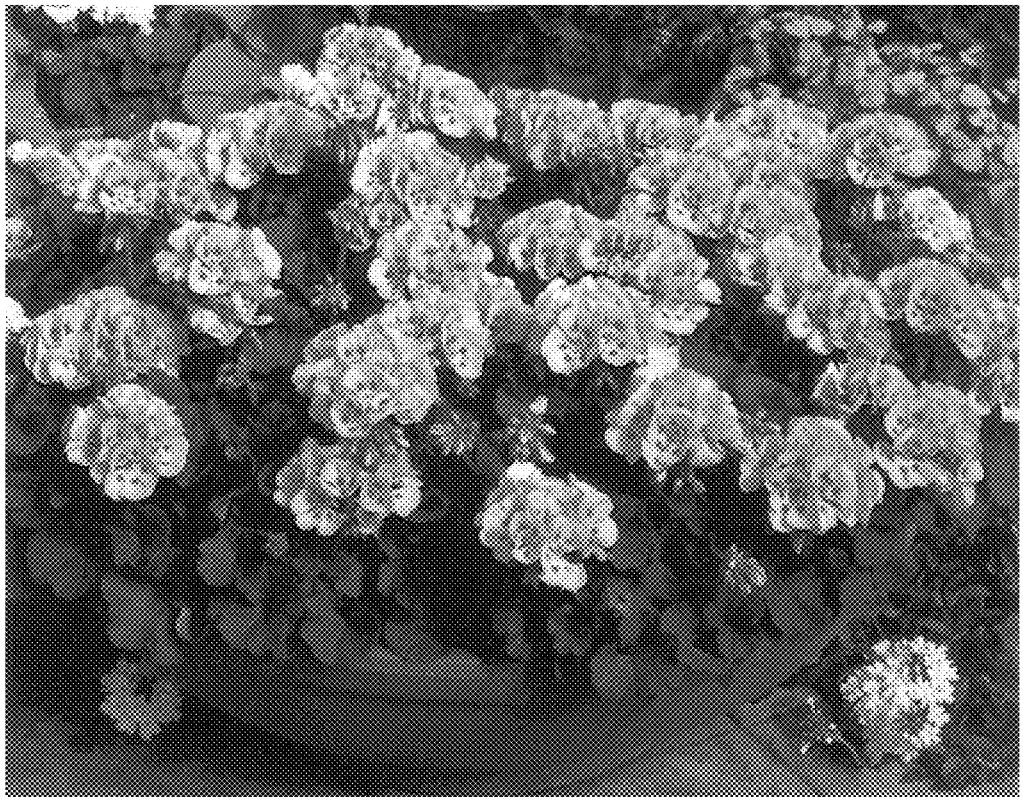

'Amri Light Pink Spla II'.

BACKGROUND OF THE NEW PLANT

The present invention comprises a new and distinct cultivar of geranium, botanically known as *Pelargonium hortorum* Bailey, and hereinafter referred to by the cultivar name 'Amri Light Pink Spla II'. The new cultivar is propagated from a seedling resulting from the cross of Melody (U.S. Plant Pat. No. 8,006), a pink flowered geranium and an unnamed and unpatented proprietary line known as 4131-1 which is a light lavender with rose spot pattern flower.

'Amri Light Pink Spla II' is a product of a planned breeding program intended to create new geranium cultivars with light pink colored flowers, semi-double flower form, dark green foliage, vigorous growth and superior cutting productivity.

The new cultivar was created in 1996 in Gilroy, Calif. and has been repeatedly asexually reproduced by cuttings in Gilroy, Calif. and Guatemala over a four and a half year period. It has also been trialed at Gilroy, Calif., Okemos, Mich. and Andijk, The Netherlands. It has been found to retain its distinctive characteristics through successive propagations; and this novelty is firmly fixed.

DESCRIPTION OF PHOTOGRAPH

This new geranium plant is illustrated by the accompanying photograph which shows blooms, buds, and foliage of the plant in full color, the colors shown being as true as can be reasonably obtained by conventional photographic procedures.

FIG. 1 shows overall plant habit.

DESCRIPTION OF THE NEW CULTIVAR

The following detailed descriptions set forth the distinctive characteristics of 'Amri Light Pink Spla II'. The data which defines these characteristics were collected from asexual reproductions carried out in Gilroy, Calif. The plant history was taken on five month old plants grown in 8 inch pots, blossomed under natural light in a greenhouse and color readings were taken in the greenhouse in Gilroy, Calif. Color references are primarily to The R.H.S. Colour Chart of The Royal Horticultural Society of London (R.H.S.).

DETAILED BOTANICAL DESCRIPTION

Classification:
*Botanical.*—*Pelargonium hortorum* Bailey.
*Commercial.*—Geranium.
Form: Upright, rounded, basal branched plant.
Height:
*From soil level to top of plant* (*excluding blooms*).—11–13 cm.
*From soil level to top of umbels.*—21–24 cm.
Width: 30–34 cm.
Time to produce a finished flowering plant: 12 weeks.
Outdoor plant performance: Good heat tolerance, strong growth, maintains rounded habit.
Time to initiate roots: 7–8 days.
Time to develop roots: 25 days.
Root description: White, slightly pubescent, fibrous yet coarse.

The Leaves

Length: 4.5–6.5 cm.
Width: 7.3–10.5 cm depending on age.
Apex measurement: 5.0 cm.
Base measurement: 7.0–7.5 cm.
Shape: Reniform, with occasional upfolding between veins.
Margin: Crenate.
Texture: Leathery and pubescent on both surfaces.
Ribs and veins: Palmate (digitate), 2.5–5.0 cm long.
Color:
*Upper side.*—Yellow-green RHS 146A.
*Under side.*—Yellow-green RHS 146B.
*Ribs.*—Yellow-green RHS 146D.
*Veins.*—Yellow-green RHS 146D.
Petiole length: 4.0–8.0 cm depending on age of the leaf.
Petiole diameter: 2.0–3.0 mm.
Petiole color: Yellow-green RHS 144A.
Lateral branch length: 4.0–8.0 cm.
Internode length: 1.0–1.7 cm.

Lateral branch color: A color of yellow-green between RHS 144A and 144B.

The Bud

Diameter: 7 mm.
Length: 1.4 cm.
Shape: Elliptic.
Color when sepals first divide: Light pink RHS 73D with darker pink RHS 73B margins.
Number of sepals: 5.
Length of sepals: 1.1–1.2 cm.
Width of sepals: 3.5 mm.
Apex shape: Cuspidate.
Base shape: Truncate.
Sepal color in an open flower: Upper and lower are yellow-green RHS 144A.

The Flower

Bloom season: Continuous throughout the year in greenhouse or Zone 9 climate.
Size: Approximately 5 cm in diameter.
Form: Polypetalous, cup shaped, later flattening to shallow cup shape.
Petals/petaloids: 5 petals, 1–2 petaloids; Shape: spatulate.
Apex shape: Obtuse.
Base shape: Attenuate.
Margin: Entire, slightly undulating.
Petal color:
*Upper surface.*—Light pink RHS 75B with a white RHS 155D eye at base, a macule of red-purple RHS 57B and stripes of red-purple RHS 57C over the white eye.
*Lower surface.*—Light pink RHS 75D with faint stripes of red-purple RHS 57C.
Surface texture of petals and petaloids: Smooth.
Petaloid color: Upper and lower surface — light pink RHS 75B.
Color change with age: Minimal.
Pedicel length: Approximately 2.5 cm.
Pedicel color: Yellow-green RHS 145A.
Flower persistence: An open flower will hold it's petals until the flower begins to dehisce, or approximately 7–10 days.

The Inflorescence

Type: An umbel composed of approximately 20 flowers.
Diameter: 9.0–10.0 cm.
Depth: 6.0 cm.
Peduncle length: 10.5–13.5 cm.
Peduncle color: Yellow-green RHS 144A.

The Reproductive Organs

Anthers: 10.
Anther color: Red RHS 48B prior to anthesis.
Filament color: White RHS 155D.
Lengths of anthers and filaments: Anther — 0.3 cm; filament 0.4–0.5 cm.
Pollen amount and color: Moderate orange RHS 24A.
Pistil: 1 with a length of 9 mm.
Stigma: 5 linear lobes with a color of pink RHS 57D.
Style: 3.5 mm with a color of pink RHS 57D.
Ovary: At anthesis, densely pubescent with white hairs, oblong, green drying to a light brown at maturity.
Seed number: Maximum of 5 per spike.
Seed length: 4–5 mm.
Seed width: 1.5–2.0 mm.
Seed color: Brown RHS 165A, may darken with age.

Disease and Insect Resistance

No susceptibility to diseases or insects noted to date.

Comparison with Known Cultivars

When 'Amri Light Pink Spla II' is compared to 'Melody', the present plant has a much lighter pink flower color than 'Melody' and also has a mcaule pattern which 'Melody' does not have. Compared to 4134-1, 'Amri Light Pink Spla II' has a more pink flower as compared to the lavender flower color of 4134-1 and also exhibits a stronger growth habit.

I claim:

1. A new and distinct cultivar of geranium plant as shown and described herein.

* * * * *